United States Patent [19]

Motley

[11] Patent Number: 5,552,136
[45] Date of Patent: Sep. 3, 1996

[54] GEL STICK COMPOSITIONS COMPRISING OPTICALLY ENRICHED GELLANTS

[75] Inventor: Curtis B. Motley, West Chester, Ohio

[73] Assignee: The Procter & Gamble Company, Cincinnati, Ohio

[21] Appl. No.: 248,938

[22] Filed: May 25, 1994

[51] Int. Cl.$^6$ .................................. A61K 7/38; A61K 7/32
[52] U.S. Cl. ............................ 424/68; 424/65; 424/400; 424/401; 424/DIG. 5; 514/944; 514/947
[58] Field of Search ................................ 424/68, 65, 400, 424/401; 514/944, 947

[56] References Cited

U.S. PATENT DOCUMENTS

| | | | |
|---|---|---|---|
| 3,499,963 | 3/1970 | Rubino | 424/157 |
| 3,553,316 | 1/1971 | Rubino | 424/68 |
| 3,734,940 | 5/1973 | Rubino | 260/448 B |
| 3,969,087 | 7/1976 | Saito et al. | 44/7 C |
| 4,425,328 | 1/1984 | Nabial | 424/68 |
| 4,666,710 | 5/1987 | Clarkson | 424/66 |
| 4,725,432 | 2/1988 | May | 424/66 |
| 4,985,238 | 1/1991 | Tanner et al. | 424/66 |
| 5,066,487 | 11/1991 | Morelle et al. | 424/68 |
| 5,302,381 | 4/1994 | Greczyn et al. | 424/66 |

FOREIGN PATENT DOCUMENTS

| | | | |
|---|---|---|---|
| 63-91311 | 4/1988 | Japan | A61K 7/00 |
| 1-207223 | 8/1989 | Japan | A61K 7/02 |
| 2-180805 | 7/1990 | Japan | A61K 7/00 |
| 1-234250 | 4/1991 | Japan. | |
| WO93-23008 | of 0000 | WIPO. | |

OTHER PUBLICATIONS

P. Terech, "Small-angle-scattering study of 12-hydroxystearic physical organogels and lubricating greases", 269, *Colloid & Polymer Science*, pp. 490–500 (1991).

McGhie et al., "Conversion of (+)-ricinoleic acid into (−)-ricinoleic acid", Communications to the Editor, Sep. 18, 1982, pp. 719–720, *Chemistry & Industry*.

Tachibana et al., "The Sense of Twist in the Fibrous Aggregates from 12-Hydroxystearic Acid and Its Alkali Metal Soaps", Letter to the Editor, *J. of Colloid and Interface Science*, vol. 28, No. 1, pp. 173–174, (1968).

Tachibana et al., "Studies of Helical Aggregates of Molecules I. Enantiomorphism in the Helical Aggregates of Optically Active 12-Hydroxystearic Acid and its Lithium Salt.", *Bulletin of the Chemical Society of Japan*, vol. 42, No. 12, pp. 3422–3424, (1969).

Tachibana et al., "Studies of Helical Aggregates of Molecules II. The Sense of Twist in the Fibrous Aggregates form the Alkali Metal Soaps of Optically Active 12-Hydroxystearic Acid", *Bulletin of the Chemical Society of Japan*, vol. 43, No. 8, pp. 2418–2421, (1970).

Tachibana et al., "Studies of Helical Aggregates of Molecules III. The Bivalent Metal Soaps of Optically Active 12-Hydroxyoctadecanoic Acid", *Bulletin of the Chemical Society of Japan*, vol. 45, No. 2, pp. 415–422, (1972).

Tachibana et al., "Chiral Mesophases of 12-Hydroxyoctadecanoic Acid in Jelly and in the Solid State. I. A New Type of Lyotropic Mesophase in Jelly with Organic Solvents", *The Chemical Society of Japan*, vol. 53, pp. 1714–1719, (1980).

Tachibana et al., "Chiral Mesophases of 12-Htdroxyoctadecanoic Acid in Jelly and in the Solid State. II. A New Type of Mesomorphic Solid State", *The Chemical Society of Japan*, vol. 54, pp. 73–80, (1981).

Vaughan, "Solubility Effects in Product, Package, Penetration, and Preservation", *Cosmetics & Toiletries*, vol. 103, pp. 47–69, (1988).

Hanabusa et al., "Small Molecular Gelling Agents to Harden Organic Liquids: Alkylamide of N-Benzyloxycarbonyl-L-Valyl-L-Valine", *J. Chem. Soc., Chem. Commun.*, pp. 390–391, (1993).

*Primary Examiner*—Shelley A. Dodson
*Attorney, Agent, or Firm*—John M. Howell; David L. Suter; Jacobus C. Rasser

[57] ABSTRACT

The subject invention relates to antiperspirant gel stick compositions comprising:
  (a) an antiperspirant active;
  (b) a gelling agent comprising:
    (i) an optically enriched primary gellant selected from the group consisting of 12-hydroxystearic acid, esters of 12-hydroxystearic acid, amides of 12-hydroxystearic acid, and mixtures thereof; and
    (ii) a secondary gellant selected from the group consisting of n-acyl amino acid amide derivatives;
  (c) a liquid base material having a solubility parameter of 9 or below;
wherein the gel stick has a hardness of 75 grams of force or more.

19 Claims, No Drawings

GEL STICK COMPOSITIONS COMPRISING OPTICALLY ENRICHED GELLANTS

FIELD OF THE INVENTION

The subject invention relates to gel stick compositions useful in preventing perspiration and body odors. Specifically, the subject invention relates to low-aqueous antiperspirant and/or deodorant compositions in the form of a gel stick.

BACKGROUND OF THE INVENTION

Personal hygiene habits typically include a means for reducing human body odors. These habits include routine bathing or washing of the body, particularly the axilla, and treating the axilla with compositions, such as antiperspirant or deodorant compositions, to retard odor formation.

Antiperspirants and deodorants generally include an astringent material in a suitable carrier. Astringent materials typically used are metal salts, particularly aluminum and zirconium metal complexes. Exemplary metal salts are disclosed in Plechner, Antiperspirants and Deodorants, 2 Cosmetics, Science and Technology, Balsam and Sagarin, 374–400, 1972; incorporated herein by reference.

Antiperspirant and deodorant compositions can be formulated in a variety of ways, each dependent on the particular ingredients involved. Such formulations include lotions, solid sticks, and creams. Solid stick formulations include gel sticks, which contain a liquid material and gelling agents.

One significant disadvantage of typical gel stick compositions is a tendency of the liquid material to escape or leak from the gel network. This leaking of the liquid material can result in reduced efficacy of the actives, poor gel formation and lower gel stability over time of any gel which is formed. The leaking may also cause processing difficulties at the temperatures and holding times typically encountered during manufacture. Gel stick compositions may have additional disadvantages such as a wet, cold and sticky feel on the skin, skin irritation, and shrinkage and containment problems due to high volatility.

It is an object of the subject invention to provide harder low-aqueous gel stick compositions.

It is a further object of the subject invention to provide low-aqueous gel stick compositions with superior gel formation.

SUMMARY OF THE INVENTION

The subject invention involves low-aqueous gel stick compositions comprising:

(a) an antiperspirant active;
(b) a gelling agent comprising:
 (i) an optically enriched primary gellant selected from the group consisting of 12-hydroxystearic acid, esters of 12-hydroxystearic acid and amides of 12-hydroxystearic acid; and
 (ii) a secondary gellant selected from the group consisting of n-acyl amino acid amide derivatives; and
(c) a liquid base material;
wherein the gel stick has a hardness of 75 grams of force or above.

DETAILED DESCRIPTION OF THE INVENTION

As used herein, the term "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indicated, preferred alkyl are as follows. Preferred alkyl are straight or branched chain, more preferably straight chain. Preferred alkyl are mono-, di-, or trisubstituted, more preferably monosubstituted or unsubstituted, most preferably unsubstituted. Preferred alkyl are $C_1$ to $C_{26}$, more preferably $C_6$ to $C_{22}$, more preferably still $C_{12}$ to $C_{18}$.

As used herein, "substituted", in reference to alkyl groups, means such groups that can be mono- or polysubstituted. Preferred substituents are selected from the group consisting of halogen, hydroxy, amino, nitro, carboxy, thio, aryl, alkyl, alkoxy, and aryloxy. More preferred substituents include alkyl, alkoxy and aryl. As used herein, the term "aryl" means aromatic rings which may be unsubstituted or substituted. Preferred aryl are phenyl or naphthyl, especially phenyl. Preferred aryl are mono-, di- or tri- substituted, or unsubstituted; more preferred aryl are monosubstituted or unsubstituted. Preferred aryl substitutents include alkyl, halo, amino, hydroxy, alkoxy, cyano, nitro and trifluoromethyl.

As used herein, the term "alkoxy" means O-alkyl.

As used herein, the term "aryloxy" means O-aryl.

Antiperspirant Active

The compositions of the subject invention contain an astringent antiperspirant active. Antiperspirant actives useful in the subject invention are well known in the art. See e.g. "Antiperspirants and Deodorants", *Cosmetic Science and Technology Series*, K. Laden & C. Felger, eds., Vol. 7., pp. 42–56 (1988); incorporated herein by reference. These actives are used at levels from about 0.5% to about 60% of the composition, preferably from about 5% to about 35%, of the gel stick composition. These weight percentages are calculated on an anhydrous metal salt basis (exclusive of complexing agents).

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y \cdot XH_2O$ wherein:

(a) Q is chlorine, bromine or iodine;
(b) x is from about 2 to about 5, and x+y=about 6, and x and y do not need to be integers; and
(c) X is from about 1 to about 6.

Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975; both incorporated herein by reference.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein:
(a) z may vary from about 0.9 to about 2 and need not be an integer;
(b) n is the valence of B;
(c) 2-nz is greater than or equal to 0:
(d) B is selected from the group consisting of halides, nitrate, sulfamate, sulfate, and mixtures thereof.

Although only zirconium compounds are exemplified in this specification, other Group IVB metal compounds, including hafnium, can be used in the subject invention.

As with the basic aluminum compounds, the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by
(A) co-dissolving in water
  (1) one part $Al_2(OH)_{6-m}Q_m$, wherein Q is an anion selected from the group consisting of chloride, bromide and iodide, and m is a number from about 0.8 to about 2.0;
  (2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;
  (3) p parts neutral amino acid selected from the group consisting of glycine, dl-tryptophane, dl-b-phenylalanine, dl-valine, valine, dl-methionine and b-alanine, and where p has a value of from about 0.06 to about 0.53;
(B) co-drying the resultant mixture to a friable solid; and
(C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl \cdot 2H_2O$. Preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_2 \cdot nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued Apr. 12, 1977, to Rubino; incorporated herein by reference.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from an aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula $[Al_2(OH)_4Cl][H_2CNH_2COOH]$.

Of all the above types of antiperspirant actives, preferred compounds include the 5/6 basic aluminum salts of the empirical formula $Al_2(OH)_5Cl \cdot 2H_2O$; mixtures of $AlCl_3 \cdot 6H_2O$ and $Al_2(OH)_5Cl \cdot 2H_2O$ with aluminum chloride to aluminum hydroxychloride weight ratios of up to about 0.5; ZAG type complexes wherein the zirconium salt is $ZrO(OH)Cl \cdot 3H_2O$, the aluminum salt is $Al_2(OH)_5Cl \cdot 2H_2O$ or the aforementioned mixtures of $AlCl_3 \cdot 6H_2O$ and $Al_2(OH)_5 Cl \cdot 2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a \cdot nH_2O$ wherein a is from about 1.5 to about 1.87 and n is from about 1 to about 7, the aluminum salt is $Al_2(OH)_5Cl \cdot 2H_2O$, and the amino acid is glycine.

The active may be incorporated either in solubilized or particulate form. Reduction in the amount of interaction between the antiperspirant active and the gelling agent results in better gel stick compositions. This interaction can be reduced by decreasing the surface area of the antiperspirant active; thereby reducing the interaction sites. The antiperspirant active is preferably in particulate form wherein the surface area of the active is relatively low. The surface area of the antiperspirant active can be reduced by increasing the size and density of the active particles. The particulate antiperspirant active preferably has a density which is greater than about 0.7 g/cm$^3$ and an average particle size (as measured by a Coulter Multisizer 11 manufactured by Coulter Corporation, Haleah, Fla.) greater than about 10 microns; more preferably, greater than about 30 microns; and most preferably, greater than about 40 microns. Such preferred materials can be purchased from Westwood Chemical Company, Middletown, N.Y. under the trade name Westchlor ZR. Suitable antiperspirant actives are disclosed, for example, in U.S. Pat. No. 4,147,766 which issued on Apr. 3, 1979 to Kozischek.

Solubilized antiperspirant actives which may be utilized in the subject invention are also well known in the art. These materials utilize monohydric or polyhydric alcohols or water to solublize the antiperspirant active before it is incorporated into the product. The levels of these polar solvents is less than 25%, and preferably less than 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 published Dec. 14, 1988; all incorporated herein by reference.

Gelling Agent

The subject compositions also comprise a gelling agent. The level of the gelling agent is typically from about 1% to about 15% of the composition; preferably, from about 3% to about 12%; more preferably, from about 5% to about 10%. As used herein, the term "gelling agent" means a mixture of a primary gellant and a secondary gellant.

As used herein, the term "primary gellant" means a compound with one chiral carbon selected from the group consisting of 12-hydroxystearic acid, esters of 12-hydroxystearic acid, amides of 12-hydroxystearic acid and mixtures thereof, having the structure:

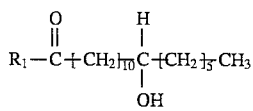

wherein:

(a) $R_1$ is $OR_2$ or $NR_2R_3$; and (b) $R_2$ and $R_3$ are, independently, hydrogen, alkyl, or aryl. At least one of $R_2$ or $R_3$ is preferably a hydrogen atom.

The primary gellant is preferably selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butylamide of 12-hydroxystearic acid, benzylamide of 12-hydroxystearic acid, phenylamide of 12-hydroxystearic acid, t-butylamide of 12-hydroxystearic acid, cyclohexylamide of 12-hydroxystearic acid, 1-adamantylamide of 12-hydroxystearic acid, 2-adamantylamide of 12-hydroxystearic acid, diisopropylamide of 12-hydroxystearic acid, and mixtures thereof; even more preferably, 12-hydroxystearic acid, isopropyl amide of 12-hydroxystearic acid, and mixtures thereof. 12-hydroxystearic acid is the most preferred primary gellant.

In the subject invention, the primary gellant is used in an optically enriched form. As used herein "optically enriched" means a primary gellant sample wherein the ratio of R isomer: S isomer or S isomer: R isomer is from about 0%: 100% to about 45%: 55%; preferably 0%: 100% to about 30%: 70%; more preferably from about 0%: 100% to about 15%: 85%; more preferably still from about 0%: 100% to about 5%: 95%; most preferably 0%: 100%.

It has been unexpectedly found that when an optically enriched sample of primary gellant is used in the subject invention, superior gelling results. While not limited to any particular mechanism of action, it is believed that the optically enriched primary gellant, in the presence of the secondary gellant, is thermodynamically favored to form to form twisted fibrils that are aligned and bundle, thereby contributing to a more ordered macro structure in which the liquid base is trapped. The racemic mixture (which comprises a 50:50 ratio of R:S), on the other hand, is thermodynamically favored to form crystals.

As used herein, the term "secondary gellant" means an n-acyl amino acid derivative. Preferred secondary gellants include n-acyl amino acid amides and n-acyl amino acid esters. Preferred secondary gellants are prepared from glutamic acid, alanine, lysine, glutamine, aspartic acid and mixtures thereof. Both d and l amino acids are effective in the subject invention; however, natural amino acids (l isomers) are preferred. Preferred secondary gellants include n-acyl glutamic acid amides and n-acyl glutamic acid esters having the structure:

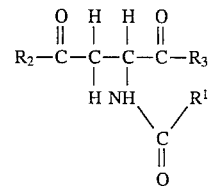

wherein:

(a) $R_1$ is alkyl, or aryl;

(b) $R_2$ and $R_3$ are, independently, alkyl, or aryl ester or amide; $R_2$ and $R_3$ are preferably the same.

Preferred secondary gellants include N-lauroylglutamic acid diethylamide, N-lauroylglutamic acid dibutylamide, N-lauroylglutamic acid dihexylamide, N-lauroylglutamic acid dioctylamide, N-lauroylglutamic acid didecylamide, N-lauroylglutamic acid didodecylamide, N-lauroylglutamic acid ditetradecylamide, N-lauroylglutamic acid dihexadecylamide, N-lauroylglutamic acid distearylamide, N-stearoylglutamic acid dibutylamide, N-stearoylglutamic acid dihexylamide, N-stearoylglutamic acid diheptylamide, N-stearoylglutamic acid dioctylamide, N-stearoylglutamic acid didecylamide, N-stearoylglutamic acid didodecylamide, N-stearoylglutamic acid ditetradecylamide, N-stearoylglutamic acid dihexadecylamide, N-stearoylglutamic acid distearylamide and mixtures thereof. More preferred secondary gellants include n-lauroylglutamic acid dibutylamide, n-stearylglutamic acid dihexylamide, and mixtures thereof.

The primary gellant: secondary gellant ratio is typically between about 1:2 and about 20:1; preferably, from about 1:1 to about 10:1; more preferably, from about 2:1 to about 7:1; and even more preferably, from about 3:1 to about 5:1.

The presence of a secondary gellant offers significant benefits when used in an antiperspirant gel stick, such as decreased residue upon application to the skin, increased hardness and better aesthetics, relative to a similar composition having either of the two gellants alone. The primary and secondary gellants are, in combination, more effective than either alone so that the overall level of gelling agent within the composition can be reduced while maintaining such desirable stick characteristics.

Liquid Base Material

A liquid base matrix of antiperspirant stick compositions of the subject invention is formed by combining the gelling agent with a liquid base material. As used herein, the term "liquid" refers to materials which are liquids at ambient conditions and the term "liquid base material" includes all liquids within the composition.

The liquid base material of the subject invention is preferably used at levels from about 10% to about 95% of the subject compositions; and more preferably from about 45% to about 80%. The liquid base material preferably includes a volatile, non-polar, oil and a non-volatile, relatively polar co-solvent.

The non-polar, volatile oil tends to impart highly desirable aesthetic properties to the gel stick and is preferably used at levels from about 10% to about 70% of the composition; more preferably, from about 25% to about 60%; more preferably from about 40% to about 60%. The term "non-polar" typically means that the emollient has a solubility parameter below about 6.5.

Particularly useful non-polar, volatile oils include silicone oils, hydrocarbons, and mixtures thereof. Such non-polar, volatile oils are disclosed, for example, in Cosmetics, Science, and Technology, Vol. 1, 27–104 edited by Balsam and Sagarin, 1972, incorporated herein by reference. The non-polar, volatile oils useful in the present invention may be saturated or unsaturated, straight or branched chained, aliphatic or aromatic. Preferred non-polar, volatile hydrocarbons include isodecane (such as Permethyl-99A®, available from Presperse Inc.) and the $C_7$-$C_8$ through $C_{12}$-$C_{15}$ isoparaffins (such as the Isopar® Series available from Exxon Chemicals).

Non-polar, volatile silicone oils are highly preferred because they provide the gel stick composition with highly desirable aesthetics. Non-polar, volatile liquid silicone oils are disclosed in U.S. Pat. No. 4,781,917 issued to Luebbe et al., on Nov. 1, 1988; and in Todd et al., "Volatile Silicone Fluids for Cosmetics", Cosmetics and Toiletries, 91:27–32 (1976); both incorporated herein by reference. Particularly preferred volatile silicone oils include cyclic volatile silicones corresponding to the formula:

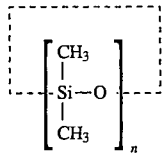

wherein n is from about 3 to about 7; and linear volatile silicones corresponding to the formula:

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200®, Dow Corning 244®, Dow Corning 245®, Dow Corning 344®, and Dow Corning 345®, (commercially available from Dow Corning Corp.); SF-1204® and SF-1202® Silicone Fluids (commercially available from G.E. Silicones), GE 7207® and 7158® (commercially available from General Electric Co.); and SWS-03314® (commercially available from SWS Silicones Corp.).

The term "non-volatile" as used herein refers to materials which exhibit a vapor pressure of no more than about 2mm Hg at 25° C. at one atmosphere and/or to materials which have a boiling point at one atmosphere of at least about 300° C. The phrase "relatively polar" as used herein means more polar than another material in terms of solubility parameter; i.e., the higher the solubility parameter the more polar the liquid. The relatively polar co-solvent of the subject invention aids in the utilization of reduced processing temperatures by solubilizing at least one of the gellants and being soluble in the non-polar, volatile oil when subjected to reduced processing temperatures. In addition to enabling reduced processing temperatures, the co-solvent enables the inclusion of greater amounts of the non-polar, volatile oil. This is advantageous because, as discussed above, the non-polar, volatile oil provides significant cosmetic benefits. The non-volatile co-solvent is "relatively polar" as compared to the non-polar, volatile oil discussed above. Therefore, the non-volatile co-solvent is more polar (i.e., has a higher solubility parameter) than at least one of the non-polar, volatile oils.

The quantity of relatively polar, non-volatile co-solvent is preferably kept to a minimum because it tends to adversely affect product cosmetics. The relatively polar, non-volatile co-solvent is preferably included at levels from about 5% to about 60% of the composition; more preferably from about 5% to about 25%; and most preferably from about 7% to about 20%.

Relatively polar, non-volatile liquids useful as the co-solvent in the subject invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989; all incorporated herein by reference. Relatively polar, non-volatile co-solvents useful in the subject invention preferably include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the subject invention may be either saturated or unsaturated, have an aliphatic character and be straight or branched chained or contain aliphatic rings or aromatic rings.

More preferably, the relatively polar, non-volatile liquid co-solvents include fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

More preferred relatively polar, non-volatile liquid co-solvents include propoxylated ethers of $C_{14}$-$C_{18}$ fatty alcohols having a degree of propoxylation below about 50, esters of $C_2$-$C_8$ alcohols and $C_{12}$-$C_{26}$ carboxylic acids (e.g. ethyl myristate, isopropyl palmitate), esters of $C_{12}$-$C_{26}$ alcohols and benzoic acid (e.g. Finsolv TN supplied by Finetex), diesters of $C_2$-$C_8$ alcohols and adipic, sebacic, and phthalic acids (e.g., diisopropyl sebacate, diisopropyl adipate, di-n-butyl phthalate), polyhydric alcohol esters of $C_6$-$C_{26}$ carboxylic acids (e.g., propylene glycol dicaprate/dicaprylate, propylene glycol isostearate); and mixtures thereof.

Even more preferred relatively polar, non-volatile liquid co-solvents include branched-chain aliphatic fatty alcohols having from about 12–26 carbon atoms, such as isocetyl alcohol, octyldecanol, octyldodecanol and undecylpentadecanol. Octyldodecanol is most preferred. Such preferred aliphatic fatty alcohols are particularly useful in combination with the volatile liquid silicone oils discussed herein to adjust the average solubility of the liquid base material.

In addition to the liquids discussed above, the liquid base material may optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989; all incorporated herein by reference. The non-volatile silicone oils useful in the present invention are essentially non-volatile polysiloxanes, paraffinic hydrocarbon oils, and mixtures thereof. The polysiloxanes useful in the subject invention include polyalkylsiloxanes, polyarylsiloxanes, polyalkylarylsiloxanes, polyethersiloxane copolymers, and mixtures thereof. Examples of these include polydimethyl siloxanes having viscosities of from about 5 to about 100,000 centistokes at 25° C.

Among the preferred non-volatile silicone emollients useful in the subject compositions are the polydimethyl siloxanes having viscosities from about 2 to about 400 centistokes at 25° C. Such polyalkylsiloxanes include the Viscasil® series (sold by General Electric Company) and the Dow Corning 200® series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid® (sold by General Electric Company) and 556 Cosmetic Grade Fluid® (sold by Dow Corning Corp.). Useful poly-ethersiloxane copolymers include, for example, a polyoxyalkylene ether copolymer having a viscosity of about 1200 to 1500 centistokes at 25° C. Such a fluid is available as SF1066® organosilicone surfactant (sold by General Electric Company). Polysiloxane ethylene glycol ether copolymers are preferred copolymers for use in the subject compositions.

Non-volatile paraffinic hydrocarbon oils useful in the subject invention include mineral oils and certain branched-chain hydrocarbons. Examples of these fluids are disclosed in U.S. Pat. No. 5,019,375 issued to Tanner et al. on May 28, 1991, incorporated herein by reference. Preferred mineral oils have the following properties: viscosity from about 5 centistokes to about 70 centistokes at 40° C.; density between about 0.82 and 0.89 g/cm$^3$ at 25° C.; flash point between about 138° C. and about 216° C.; and carbon chain length between about 14 and about 40 carbon atoms.

Preferred branched chain hydrocarbon oils have the following properties: density between about 0.79 and about 0.89 g/cm$^3$ at 20° C.; boiling point greater than about 250° C.; and flash point between about 110° C. and about 200° C.

Particularly preferred branched-chain hydrocarbons include Permethyl 103A®, which contains an average of about 24 carbon atoms; Permethyl 104A®, which contains an average of about 68 carbon atoms; Permethyl 102A®, which contains an average of about 20 carbon atoms; all of which may be purchased from Permethyl Corporation; and Ethylflo 364® which contains a mixture of 30 carbon atoms and 40 carbon atoms and may be purchased from Ethyl Corp.

The liquid base materials include emollients which have a solubility parameter from about 5 to about 9. It is preferable that, in aggregate, the average solubility parameter of the liquid base material be from about 6 to about 9. Hence, a mixture of emollients may be used as the liquid base material herein, each having a solubility parameter in the range of from about 5 to about 9, such that the average solubility parameter of the mixture is from about 6 to about 9. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 *J Soc. Cosmetic Chemists* 319–333, Sept/Oct, 1985; both incorporated herein by reference.

The liquid base material comprises at least two solvents. One solvent is preferably a silicone oil. The second solvent is preferably an organic solvent with a solubility parameter of less than 9.

It is important that the liquid base material be of a type, and used at a level sufficient to solubilize the gelling agent when heated, to permit substantially uniform mixing of the antiperspirant active into the heated solution at the mixing temperature, and form a stick when cooled to ambient temperature. The liquid base material must be compatible with the gelling agent so that the mixture of the two remains homogeneous and does not phase separate during manufacturing and so that the finished product remains homogeneous and does not phase separate at ambient conditions over the normal shelf-life which may be upwards of one year. Furthermore, the liquid base materials are typically selected to provide aesthetic benefits, such as emolliency, low tack and/or minimized visible residue, without significant interference with the effectiveness of the antiperspirant active component. The particular liquid base material should be safe for application to human skin.

Gel Sticks

As used herein, the term "stick" means a non free flowing solid with a hardness of at least 75 grams of force, more preferably at least 100 grams of force, more preferably still at least 150 grams of force, as measured by using a Steven's-LFRA Texture analyzer with a 2 mm×64 mm steel cylinder blunt tip probe at 2 mm/sec to a constant depth. The depth of measurement is typically 15 mm for samples of approximately 10 grams. For samples of approximately 3 grams, the depth is 10 mm. Three readings are taken per sample and averaged. The typical standard deviation is approximately 10 grams.

As used herein, the term "low-aqueous gel stick composition" means a gel stick composition comprising less than 50% water, preferably less than 30%, more preferably less than 20% water, even more preferably less than 10% water, also preferably less than 5% water. The most preferred gel stick compositions are substantially water free. As used herein, the term "substantially water free" means that the only water content in the formulation comes from the degrees of hydration associated with the raw materials used in the formulation.

Optional Ingredients

Antiperspirant and/or deodorant gel stick compositions of the subject invention may contain optional components which act as additional actives or modify the physical characteristics of the composition or the components making up the compositions. Such components are well known in the art. A non-limiting group of these optional components include colorants, perfumes, thickeners, distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99:55–60 (1984); all incorporated herein by reference.

Emulsifiers are particularly useful in the subject invention. The level of emulsifiers used in the subject invention is typically less than about 10% of the composition, preferably less than about 5%. These emulsifiers include non-ionic surfactants useful for forming water-in-oil emulsions. Examples of these emulsifiers include polyoxyethylene ethers of fatty alcohols, and lo polyoxyethylene-polysiloxane copolymers. Such emulsifiers are disclosed by EPO Application 373,424 Raleigh et al., and U.S. Ser. No. 530,671, Cedeno et al., filed Jul. 2, 1991; incorporated herein by reference.

Thickeners are also useful in the subject invention. Typically thickeners comprise less than about 5% of the composition. Examples of thickeners useful in the subject compositions are disclosed in U.S. Pat. No. 4,985,238, Tanner et al., issued Jan. 15, 1991; incorporated herein by reference. These thickeners include wax-like materials such as beeswax, cerasin, hydrogenated castor oil, synthetic waxes such as Fisher Tropsch® waxes, microcrystalline waxes, polyethylene waxes, and mixtures thereof.

Particulate and filler materials may also be included in the subject compositions. These materials are typically used at levels from about 0.5% to about 5% of the composition, preferably not more than 3%. Such materials are disclosed in U.S. Pat. No. 5,019,375, Tanner et al., issued May 28, 1991; incorporated herein by reference. Suitable filler materials include collodial silica (such as Cab-O-Sil®, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987; incorporated herein by reference. Examples of other particulate materials include particulate hydrophilic polymers such as cellulose ether polymers, modified starches, polyamides, and polypeptides.

A wash-off agent may be utilized to improve the ease with which the ingredients, particularly the gelling agent and the non-polar, non-volatile oils, may be washed off. The wash-off agent is preferably a non-liquid. The wash-off agent is typically in the gel stick composition in an amount from about 0.1% to about 10% of the composition.

Typical wash-off agents are non-liquids selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH2CH2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$, preferably, the polyoxyethylene ethers, wherein $R_1$ and $R_2$ are, independently, alkyl, alkenyl, or aromatic hydrocarbon which may be substituted or unsubstituted, preferably an alkyl radical, having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, Unithox-480®, Unithox-425®, and PEG-20 glyceryl stearate; more preferably, ceteareth-20, steareth-21, PEG-20 stearate, Unithox-480®, Unithox-425®, and PEG-16 hydrogenated castor oil; more preferably still, ceteareth-20, Unithox-480® and Unithox-425®; also preferably Unithox-480® and Unithox-425®.

METHODS OF MANUFACTURE

The subject compositions may be manufactured by typical methods known to those skilled in the art. See, e.g., *Gels and Sticks Formulary*, 99 Cosmetics & Toiletries 77–84, 1984; incorporated herein by reference. The following method is particularly preferred.

The gelling agent and the liquid base material are combined in a vessel equipped with a heat source. The mixture is heated to between about 80° C. and about 130° C. with stirring, until a homogeneous, molten solution is formed. Preferably, the homogeneous, molten solution is allowed to cool to a mixing temperature, typically between about 65° C. and about 120° C. Alternatively, the mixture is heated to the mixing temperature until the mixture forms a homogeneous, molten solution. This alternative method, however, typically takes longer than overheating and cooling.

The active and optional ingredients, such as fragrances and colors, are added into the homogeneous molten solution in the above vessel with stirring. The mixture is cooled until thickening occurs and poured into containers.

METHODS FOR USE

The subject invention provides methods for preventing perspiration and malodor associated with human perspiration. These methods comprise applying to the skin of a human a safe and effective amount of the gel of the subject invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram per axilla to about 1.0 gram per axilla.

EXAMPLES

The following examples further describe and demonstrate embodiments within the scope of the subject invention. These examples are solely for the purpose of illustration and are not to be construed as limitations of the present invention as many variations are possible without departing from the spirit or scope thereof.

The levels of the components in the examples below are expressed by total weight of the composition.

| Ingredient | EXAMPLE NO. | | | | | | | |
| --- | --- | --- | --- | --- | --- | --- | --- | --- |
| | 1 | 2 | 3 | 4 | 5 | 6 | 7 | 8 |
| N-Lauroyl-L-glutamic acid-di-n-butyl amide[1] | 4 | 5 | 1 | 3 | 2 | 2 | 2 | 1 |
| 12-hydroxystearic acid (100% R isomer) | 2 | 5 | 5 | 6 | 7 | 3 | 6 | 1 |
| Cyclomethicone D-5[2] | q.s. | q.s. | q.s. | q.s. | q.s. | q.s. | q.s. | — |
| Polyphenylmethylsiloxane[3] | — | — | — | 3 | — | — | 5 | — |

-continued

| | | | | | | | | |
|---|---|---|---|---|---|---|---|---|
| Light mineral oil[4] | 2 | — | — | — | — | — | — | — |
| Panalene-L-14E ®[5] | — | 15 | 10 | 11 | — | — | — | — |
| Isopropyl Myristate | — | 15 | 15 | 16 | — | — | 11 | — |
| Isopropyl Alcohol | — | — | — | — | 18 | — | — | — |
| Captex 200 ®[6] | — | — | — | — | — | 15 | — | — |
| $C_{12}$—$C_{15}$ Alcohols Benzoate[7] | — | — | — | — | — | — | 8 | — |
| PPG-3 Myristyl Ether | — | — | — | — | — | — | — | 26 |
| Diisopropyl Sebacate[8] | 43 | — | — | — | — | — | — | — |
| Aluminum Zirconium Trichlorhydrex Gly ®[9] | 25 | 20 | 20 | 20 | — | 40 | 25 | — |
| Aluminum Chlorohydrate[10] | — | — | — | — | 30 | — | — | 10 |
| EDTA | 0.2 | 0.1 | 0.5 | 1 | 5 | 10 | 7 | 0.01 |
| Talc | 3 | — | — | 2 | — | — | — | 5 |

[1]GP-1 ® supplied by Ajinomoto, Inc.
[2]Dow Corning 245 Fluid ® -cyclic polydimethylsiloxane
[3]Dow Corning 556 Fluid ®
[4]Benol White Mineral Oil supplied by Witco Chemical Corp.
[5]polyisobutene supplied by Amoco Chemical Company
[6]propylene glycol dicaprate/dicaprylate supplied by Capital City Products
[7]Finsolv TN ® supplied by Finetex
[8]Schercemol DIS ® supplied by Scher Chemicals Inc.
[9]Supplied by Westwood Chemical Co.
[10]Westchlor DM200 ® supplied by Westwood Chemical Co.

| Ingredient | EXAMPLE NO. | | | | | | | | | |
|---|---|---|---|---|---|---|---|---|---|---|
| | 9 | 10 | 11 | 12 | 13 | 14 | 15 | 16 | 17 | 18 |
| N-Lauroyl-L-glutamic acid-di-n-butyl amide[1] | 2 | 2 | 2 | 2 | 2 | 2 | 2 | 2 | 2 | 2 |
| 12-hydroxystearic acid (85% S isomer, 15% R isomer) | 6 | 6 | 6 | 6 | 6 | 6 | 6 | 6 | 6 | 6 |
| Cyclomethicone D-4[2] | q.s. | — | q.s. | — | q.s. | q.s. | q.s. | q.s. | — | — |
| Cyclomethicone D-5[3] | — | q.s. | — | q.s. | — | — | — | — | q.s. | q.s. |
| PPG-3-myristryl ether | — | — | — | — | 12 | — | — | — | — | — |
| PPG-5-butyl ether | — | — | — | — | — | 10.5 | — | — | — | — |
| PPG-10-cetyl ether | — | — | — | — | — | — | 12.5 | — | — | — |
| Isocetyl alcohol | 7 | 8 | 13 | — | — | — | — | — | — | — |
| Isostearyl alcohol | — | — | — | 13 | — | — | — | — | — | — |
| Octyldodecanol | — | — | — | — | 8.5 | — | — | — | 14 | 14 |
| Polydecene[4] | — | — | 26 | — | — | — | — | — | — | — |
| Citric Acid | 4 | 1 | 10 | 0.1 | 2 | 5 | 0.2 | 0.5 | 0.01 | 0.05 |
| Ceteareth-20 | — | — | — | — | — | — | — | — | 2.5 | 2.5 |
| Dipropyleneglycol | — | — | — | — | — | — | — | — | — | 0.25 |
| $C_{20-40}$ alcohols[5] | — | — | — | — | — | — | — | — | 0.5 | 0.5 |
| $C_{40-60}$ alcohols[6] | 0.5 | 0.5 | 0.5 | 0.5 | 0.5 | 0.5 | 0.5 | 0.5 | — | — |
| Aluminum Zirconium Trichlorhydrex Gly ®[7] | 26 | 26 | 26 | 26 | 26 | 26 | 26 | 26 | 26 | 26 |

[1]GP-1 ® supplied by Ajinomoto, Inc.
[2]Dow Corning 245 Fluid ® -cyclic polydimethylsiloxane
[3]Dow Corning 244 Fluid ® -cyclic polydimethylsiloxane
[4]Ethylflo 364 ® supplied by Ethyl Corp.
[5]Unilin 425 ® supplied by Petrolite
[6]Unilin 700 ® supplied by Petrolite
[7]Supplied by Westwood Chemical Co.

| Ingredient | EXAMPLE NO. | | | | | | |
|---|---|---|---|---|---|---|---|
| | 19 | 20 | 21 | 22 | 23 | 24 | 25 |
| N-Stearyl-L-glutamic acid-di-n-hexyl amide[1] | 2 | 2 | — | — | — | — | — |
| N-Lauroyl-L-glutamic acid-di-n-octyl amide[1] | — | — | 2 | 2 | — | — | — |
| N-Lauroyl-L-glutamic acid-di-n-decyl amide[1] | — | — | — | — | 2 | — | — |
| N-Stearyl-L-glutamic acid-di-n-decyl amide[1] | — | — | — | — | — | 2 | — |
| N-Lauroyl-L-glutamic acid-di-n-stearyl amide[1] | — | — | — | — | — | — | 2 |
| 12-hydroxystearic acid (30% R isomer, 70% S isomer) | — | — | 6 | 6 | 6 | 6 | 6 |
| Isopropyl amide of 12-hydroxystearic acid[1] (30% R isomer, 70% S isomer) | 6 | 6 | — | — | — | — | — |

| | | | | | | | |
|---|---|---|---|---|---|---|---|
| Cyclomethicone D-5[2] | q.s. | q.s. | q.s. | q.s. | q.s. | q.s. | q.s. |
| Salicylic Acid | 0.01 | 1 | 10 | 5 | 0.2 | 0.5 | 3 |
| C12–15 Alcohols Benzoate[3] | 25 | — | 25 | — | 25 | 25 | 25 |
| Octyldodecanol | — | 14 | — | 14 | — | — | — |
| Ceteareth-20 | — | 2.5 | — | 2.5 | — | — | — |
| $C_{40-60}$ alcohols[4] | 0.5 | 0.5 | 0.5 | 0.5 | 0.5 | 0.5 | 0.5 |
| Aluminum Zirconium Trichlorhydrex Gly ®[5] | 26 | 26 | 26 | 26 | 26 | 26 | 26 |

[1] Supplied by Starks Chemical Co.
[2] Dow Corning 245 ® Fluid - cyclic polydimethylsiloxane
[3] Finsolv TN ® supplied by Finetex
[4] Unilin 700 ® supplied by Petrolite
[5] Supplied by Westwood Chemical Co.

| Ingredient | EXAMPLE 26 |
|---|---|
| Octyldodecanol | 14 |
| 12-Hydroxystearic acid (100% S isomer) | 7 |
| N-Lauroyl Glutamate Dibutylamide[1] | 2 |
| Unithox 480 ® | 1.25 |
| Unithox 425 ® | 0.5 |
| Aluminum Zirconium Trichlorohydrex Gly ®[2] | 26 |
| Cyclomethicone D-5[3] | q.s. |

[1] Supplied by Starks Chemical Co
[2] Supplied by Westwood Chemical Co.
[3] Dow Corning 245 Fluid ® - cyclic polydimethylsiloxane Although particular examples of gel stick compositions of the subject invention have been described, modifications may be made without departing from the spirit and scope of the subject invention. Accordingly, the subject invention comprises all embodiments within the scope of the appended claims.

What is claimed is:

1. Antiperspirant gel composition comprising:
   a. an effective amount of an antiperspirant active
   b. an effective amount of a gelling agent, comprising:
      (i) an optically enriched primary gellant selected from the group consisting of 12-hydroxystearic acid, esters of 12-hydroxystearic acid, amides of 12-hydroxystearic acid corresponding to the formula:

$$R_4-\overset{O}{\overset{\|}{C}}-[CH_2]_{10}-\overset{H}{\overset{|}{\underset{OH}{C}}}-[CH_2]_5-CH_3$$

wherein $R_4$ is $OR_5$ or $NR_5R_6$; and $R_4$ and $R_5$ are, independently selected from the group consisting of hydrogen, alkyl moieties, aryl moieties and mixture thereof, wherein said moieties have from 1 to about 26 carbon atoms, wherein said primary gellant is the S isomer and combinations of the S isomer and R isomer of said primary gellant, wherein the ratio of S to R or R to S isomers is not less than 45%:55%;

(ii) a secondary gellant selected from the group consisting of d or l n-acyl amino acid amide derivatives corresponding to the formula:

$$R_2-\overset{O}{\overset{\|}{C}}-\overset{H}{\overset{|}{\underset{H}{C}}}-\overset{H}{\overset{|}{\underset{NH}{C}}}-\overset{O}{\overset{\|}{C}}-R_3 \quad \overset{R^1}{\underset{\underset{O}{\overset{\|}{C}}}{\diagdown\diagup}}$$

wherein $R_1$ is an alkyl moiety, aryl moiety and mixtures thereof having from about 6 to about 22 carbon atoms; and $R_2$ and $R_3$ are independently selected from the group consisting of alkyl ester, aryl ester, alkyl amide, aryl amide and mixtures thereof having from about 1 to about 26 carbon atoms; and c. an effective amount of a liquid base material having a solubility parameter of 9 or below wherein the gel stick has a hardness of 75 g of force or more.

2. The composition of claim 1 wherein the composition comprises less than 30% water.

3. The composition of claim 2 wherein the liquid base material comprises a volatile, non-polar, oil, a non-volatile, relatively polar co-solvent, and mixtures thereof.

4. The composition of claim 1 wherein the liquid base material comprises a non-polar, volatile oil selected from the group consisting of cyclic volatile silicones having the structure:

$$\left[\begin{array}{c} CH_3 \\ | \\ Si-O \\ | \\ CH_3 \end{array}\right]_n$$

wherein n is from about 3 to about 7; and linear volatile silicones corresponding to the formula:

$(CH_3)_3Si-O-[Si(CH_3)_2O]_m-Si(CH_3)_3$ wherein m is from about 1 to about 7; and mixtures thereof.

5. The composition of claim 4 wherein the composition has a hardness of 100 g of force or more and comprises less than 20% water.

6. The composition of claim 5 wherein:
   a) the primary gelling agent is 12-hydroxystearic acid; and
   b) the secondary gelling agent is in l form.

7. The composition of claim 6 wherein the secondary gelling agent is selected from the group consisting of N-lauroylglutamic acid diethylamide, N-lauroylglutamic acid dibutylamide, N-lauroylglutamic acid dihexylamide, N-lauroylglutamic acid dioctylamide, N-lauroylglutamic acid didecylamide, N-lauroylglutamic acid didodecylamide, N-lauroylglutamic acid ditetradecylamide, N-lauroylglutamic acid dihexadecylamide, N-lauroylglutamic acid distearylamide, N-stearoyl-glutamic acid dibutylamide, N-stearoylglutamic acid dihexylamide, N-stearoylglutamic acid diheptylamide, N-stearoylglutamic acid dioctylamide, N-stearoylglutamic acid didecylamide, N-stearoylglutamic acid didodecylamide, N-stearoylglutamic acid ditetradecylamide, N-stearoylglutamic acid dihexadecylamide, N-stearoylglutamic acid distearylamide and mixtures thereof.

8. The composition of claim 7 wherein the secondary gelling is selected from the group consisting of N-lauroylglutamic acid dibutylamide, N-stearylglutamic acid dihexylamide, and mixtures thereof.

9. The composition of claim 7 wherein the composition has a hardness of 150 g of force or more and comprises less than 5% water.

10. The composition of claim 9 wherein the 12-hydroxystearic acid has an (R isomer): (S isomer) or an (S isomer): (R isomer) ratio ranging from about 0%:100% to about 30%:70%.

11. The composition of claim 10 wherein:
    (a) the composition comprises from about 3% to about 12% of the gelling agent; and
    (b) the primary gellant: secondary gellant ratio is from about 1:1 to about 10:1.

12. The composition of claim 11 wherein the active is an aluminum, zirconium and amino acid complex having an Al:Zr ratio from about 1.67 to about 12.5 and a Metal:Cl ratio of from about 0.73 to about 1.93.

13. The composition of claim 12 wherein the active has an average particle size greater than about 30 microns and a density greater than about 0.7 grams per cubic centimeter.

14. The composition of claim 13 wherein the 12-hydroxystearic acid has an (R isomer:S isomer) or an (S isomer:R isomer) ratio ranging from about 0%:100% to about 15%:85%.

15. The composition of claim 14 wherein the 12-hydroxystearic acid has an (R isomer:S isomer) or an (S isomer:R isomer) ratio ranging from about 0%:100% to about 5%:95%.

16. The composition of claim 15 wherein the secondary gelling agent is selected from the group consisting of N-lauroylglutamic acid dibutylamide, n-stearylglutamic acid, dihexylamide and mixtures thereof.

17. The composition of claim 16 wherein the non-polar volatile silicone oil is cyclomethicone D-5.

18. The composition of claim 17 wherein the composition is substantially water free.

19. The composition of claim 18 wherein the primary gellant comprises either 100% R or 100% S 12-hydroxystearic acid.

* * * * *